(12) United States Patent
Meßner et al.

(10) Patent No.: US 7,226,479 B2
(45) Date of Patent: Jun. 5, 2007

(54) INTRAOCULAR LENS

(75) Inventors: Arthur Meßner, Schnaittach (DE); Ersan Özmen, Erlangen (DE); Tim Use, Nürnberg (DE)

(73) Assignee: HumanOptics AG (DE)

( * ) Notice: Subject to any disclaimer, the term of this patent is extended or adjusted under 35 U.S.C. 154(b) by 121 days.

(21) Appl. No.: 11/111,092

(22) Filed: Apr. 21, 2005

(65) Prior Publication Data

US 2005/0246017 A1    Nov. 3, 2005

(30) Foreign Application Priority Data

Apr. 30, 2004  (DE) .................... 10 2004 021 755

(51) Int. Cl.
*A61F 2/16*  (2006.01)

(52) U.S. Cl. .................... 623/6.39; 623/6.16; 623/6.43

(58) Field of Classification Search ............... 623/6.16, 623/6.38–6.4, 6.43, 6.46, 6.47, 6.49
See application file for complete search history.

(56) References Cited

U.S. PATENT DOCUMENTS

| 6,409,762 B1 | 6/2002 | Pynson et al. |
| 2002/0095212 A1 | 7/2002 | Boehm |
| 2003/0018386 A1 | 1/2003 | Laguette et al. |
| 2004/0024454 A1 | 2/2004 | Toop |

FOREIGN PATENT DOCUMENTS

| EP | 0 579 528 | 1/1994 |
| EP | 0 592 813 | 4/1994 |
| WO | WO 00/66042 | 11/2000 |
| WO | WO 02/17818 | 3/2002 |

*Primary Examiner*—William H Matthews
(74) *Attorney, Agent, or Firm*—McGlew & Tuttle, PC

(57) ABSTRACT

An intraocular lens for implantation in a capsule of an eye comprises an optic which has a substantially circular rim, an optical axis, and a lens plane that extends vertically of the optical axis; at least two haptics for support of the optic on the capsule, the haptics being fixed to the optic and forming one piece with the optic and consisting of reversibly deformable material, each haptic having a first Z-shaped haptic clamp articulated to the rim, a second Z-shaped haptic clamp articulated to the rim, and a connecting clamp which is concave in relation to the optical axis, uniting the first haptic clamp and the second haptic clamp.

12 Claims, 5 Drawing Sheets

# INTRAOCULAR LENS

BACKGROUND OF THE INVENTION

1. Field of the Invention

The invention relates to an intraocular lens for implantation in the capsule of an eye, in particular a human eye.

2. Background Art

WO 02/17818 A1 describes an intracoular lens. Two flexible legs project radially from this lens and are united by a rib. The legs and the rib have substantially the same thickness. No defined joints are provided additionally. Therefore, the compression behaviour of these haptics, upon implantation into the capsule, is not defined.

Another intraocular lens is known from U.S. Pat. No. 6,409,762 B1. It comprises two ribs which project radially from the optic and are united by a convex rib. Compressing the haptics in the radial direction result in the rib resting very rapidly on the ribs that project radially as seen in FIG. 3 of U.S. Pat. No. 6,409,762 B1. The interval of radial deformation is rather restricted.

SUMMARY OF THE INVENTION

It is an object of the invention to embody an intraocular lens that fits centrically in the capsule after implantation and adjusts easily to varying capsule diameters.

This object is attained by the features of claim 1. The gist of the invention resides in providing an optic with haptics which consist of haptic clamps in the shape of a Z and a connecting clamp uniting them. The connecting clamp is concave i.e., it is bent inwards as seen from the optical axis. The smaller the diameter of the capsule, the more the Z-shaped haptic clamps will be pressed towards the rim of the optic, the connecting clamp being simultaneously bent more strongly.

Further advantageous embodiments of the invention will become apparent from the sub-claims.

Additional features and details of the invention will become apparent from the description of an exemplary embodiment, taken in conjunction with the drawing.

DESCRIPTION OF THE PREFERRED EMBODIMENT

Figure 1:
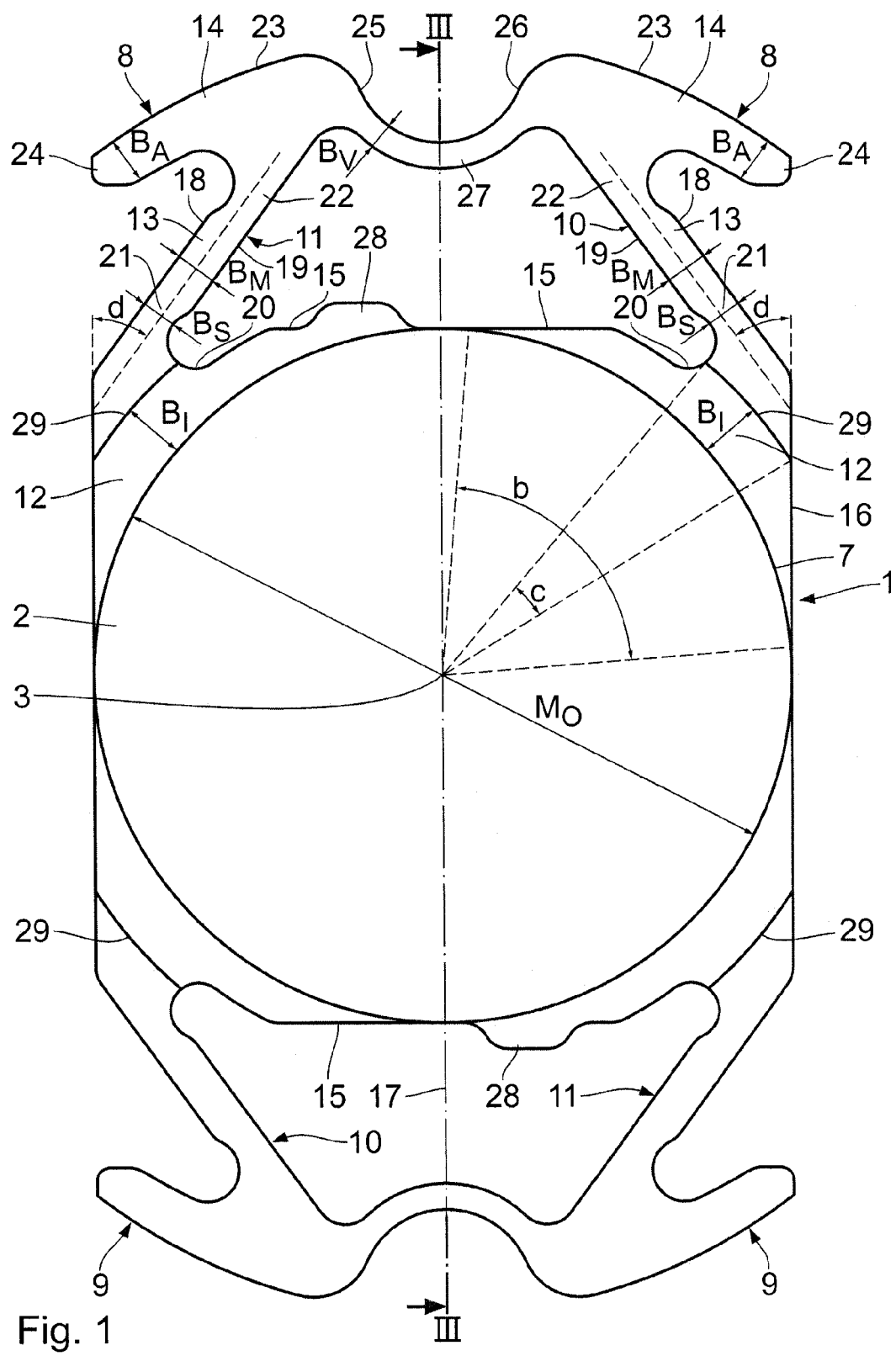
FIG. 1 is a posterior view of the intraocular lens according to the invention.

A one-piece intraocular lens 1 comprises a centric optic 2 with an optical axis 3 that extends through the center of the optic and vertically thereto. The optic further comprises a lens plane 4 that is perpendicular to the axis 3 and centric of the optic 2. The optic consists of transparent, flexible material, for example pHEMA, and possesses the properties of an optical lens. The optic 2 has a diameter $M_O$ to which applies 5 mm $\leq M_O \leq$ 8 mm, in particular $M_O \cong$ 6 mm. The optic 2 has an anterior surface 5 and a posterior surface 6. When implanted, the anterior surface 5 is turned towards the anterior chamber of the eye, whereas the posterior surface 6 is turned towards the retina. The optic 2 has a circular rim 7.

From the rim 7 of the optic 2, two haptics 8, 9 extend in opposite directions i.e., they are offset by 180° on the rim 7. The haptics 8 and 9 are point-symmetric in relation to the axis 3 i.e., the haptic 8 can pass into the haptic 9 by rotation by 180° about the axis 3. The haptics 8 and 9 serve for supporting the optic 2 in the capsule. Each haptic 8 and 9 comprises a haptic clamp 10 and a haptic clamp 11 which, in simplistic wording, are both Z-shaped, extending from the rim 7 outwards and towards one another. Along the lines of this patent, the term Z-shaped can mean a structure substantially corresponding to the shape of the letter Z, but also a structure that corresponds to the shape of a mirrored Z, in which the inclined line does not run from the top right to the bottom left, but from the top left to the bottom right. The haptic clamp 10 comprises an inner clamp 12, an adjoining central clamp 13 and an adjoining outer clamp 14. The inner clamp 12 has substantially the shape of the part of a ring that extends from part of the rim 7 outwards by an angle at center b. As for the angle b, 90° $\geq$ b $\geq$ 30° applies, in particular b $\cong$ 80°. The inner clamp 12 is defined by outer edges 15, 16 at both ends, the edges 15, 16 being substantially tangential to the rim 7. The inner clamp 12 has a central area that is united with the central clamp 13, having an angular width c to which applies 15° $\leq$ c $\leq$ 25°, in particular c $\cong$ 18°. In this area, the inner clamp 12 has a radial width $B_I$ to which $B_I \cong 0.16 \times Mo/2$ applies. As it were, the inner clamp 12 constitutes the bottom leg of the letter Z. Along the angle b, the inner clamp 12 is integrally united with the corresponding section of the rim 7.

Figure 2:
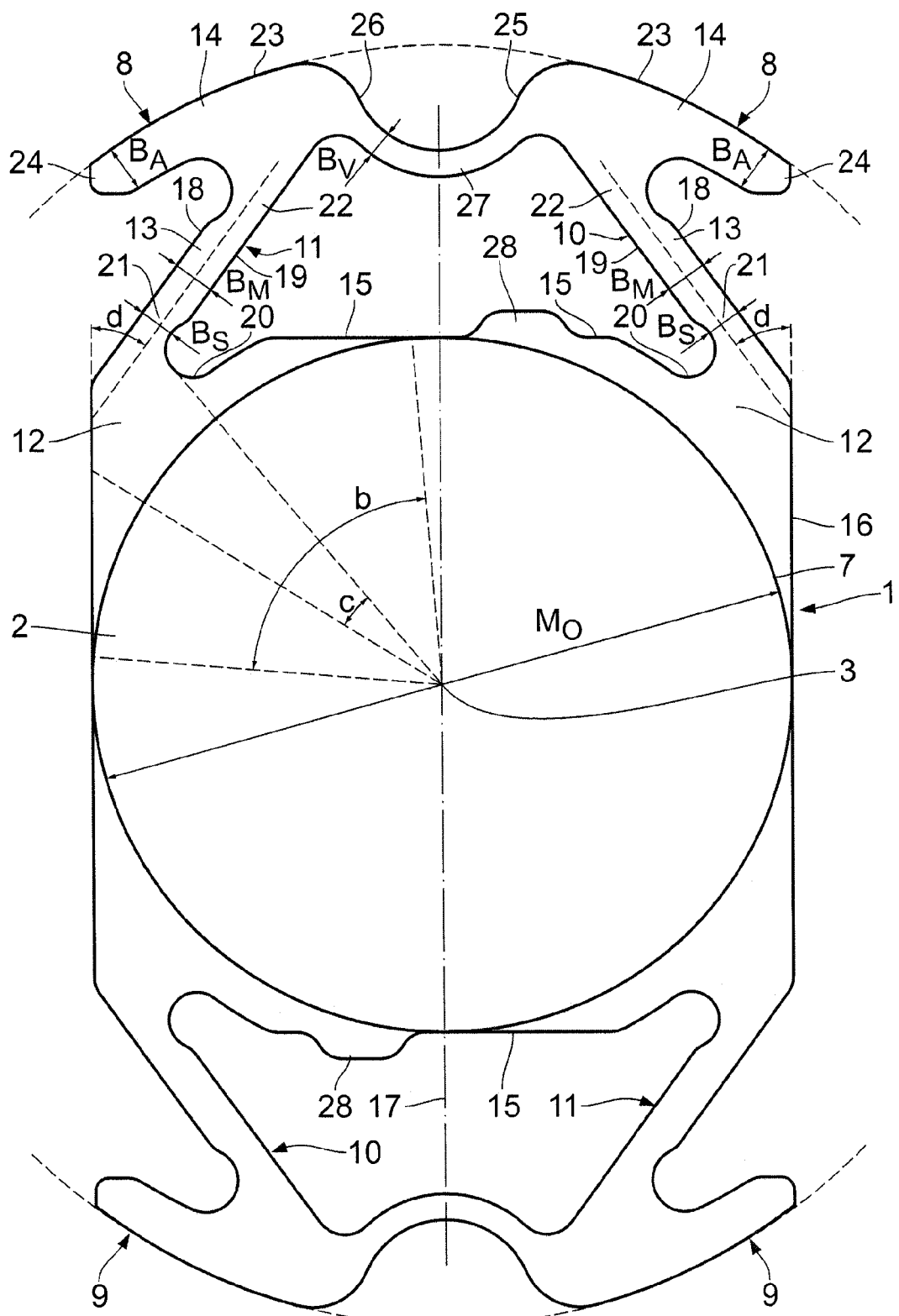
FIG. 2 is an anterior view of the intraocular lens according to FIG. 1.

From the central area of the inner clamp 12 with the angular width c, the substantially straight central clamp 13 inclines towards the cutting plane 17 seen in FIG. 1 where the optical axis 3 is located and which is perpendicular to the lens plane 4. The edge 16 which is parallel to the cutting plane 17 and the central clamp 13 make an angle d, to which applies 25° $\leq$ d $\leq$ 60°, in particular d $\cong$ 36°. The central clamp 13 comprises side walls 18, 19 which are substantially parallel to each other. The side wall 19 and the edge 15 define a semi-circular recess 20 which provides the central clamp 13, in the vicinity of its bottom end, with a pre-determined bending point 21 where the material has an inferior width $B_S$ as compared to the surrounding material. Otherwise the central clamp 13 has a width $B_M$, to which applies $B_M > B_S$. The pre-determined bending point 21 makes the job of a joint and is called the inner joint. The central clamp 13 corresponds to the inclined line of the letter Z. A pre-determined bending point 22 is located in the vicinity of the outer end of the-central clamp 13; it is called the outer joint. The width $B_S$ in the vicinity of the pre-determined bending points 21 and 22 is approximately 0.27 mm. The width of the material in the vicinity of the pre-determined bending point 22 is inferior to the width $B_M$. From the outer end of the central clamp 13, the outer clamp 14 extends in a direction away from the cutting plane 17. The outer clamp 14 corresponds to the top horizontal line of the letter Z. The outer clamp 14 possesses an outer contour 23 which lies outwards seen in the radial direction, being located on an arc about the axis 3, in particular an arc of a circle, as seen in FIG. 2. The outer clamp 14 has a projecting free end 24, the width $B_A$ of which corresponds approximately to $B_M$. The free end 24 and the central clamp 13 define a U-shaped clearance zone.

With respect to the cutting plane 17, the central clamp 13 and outer clamp 14 of haptic clamp 11 are designed on mirror-symmetry, so that reference is made to the description of the haptic clamp 10 for any details. In the view of FIG. 1, the haptic clamp 11 has the shape of a Z whereas the haptic clamp 10 has the shape of a Z mirrored on the plane 17. A connecting clamp 27 is disposed between the ends 25 and 26, turned towards the plane 17, of the two outer clamps 14. The connecting clamp 27 is concave relative to the axis 3 i.e., it is curved inwards. The clamp has a substantially constant concavity. The connecting clamp 27 has a width $B_V$, with $B_V \cong 0.2$ mm applying. The width $B_V$ of the connecting clamp 27 is inferior to the width $B_S$ of the pre-determined bending points 21, 22.

The inner clamps 12, which oppose each other as related to the plane 17, differ in that the haptic clamp 11 is provided with a projection 28 in the shape of a rib that stands out upwards from the edge 15, serving as orienting means. In the haptic 9, the projection 28 is disposed in point-symmetry of the axis 3. The projection 28 serves as orienting means, ensuring during the implantation that the surfaces 5 and 6 are not confused. Seen from behind i.e., as illustrated in FIG. 1, the projection 28 must be at the top left. In a frontal view of the lens 1 according to FIG. 2, the projection 28 is located at the top right. Any characteristic visible from outside can be used as orienting means as long as it is not disposed in mirror-symmetry of the plane 17. However, the point-symmetrical arrangement of the orienting means facilitates handling because both haptics 8 and 9 are equivalent.

Figure 3:
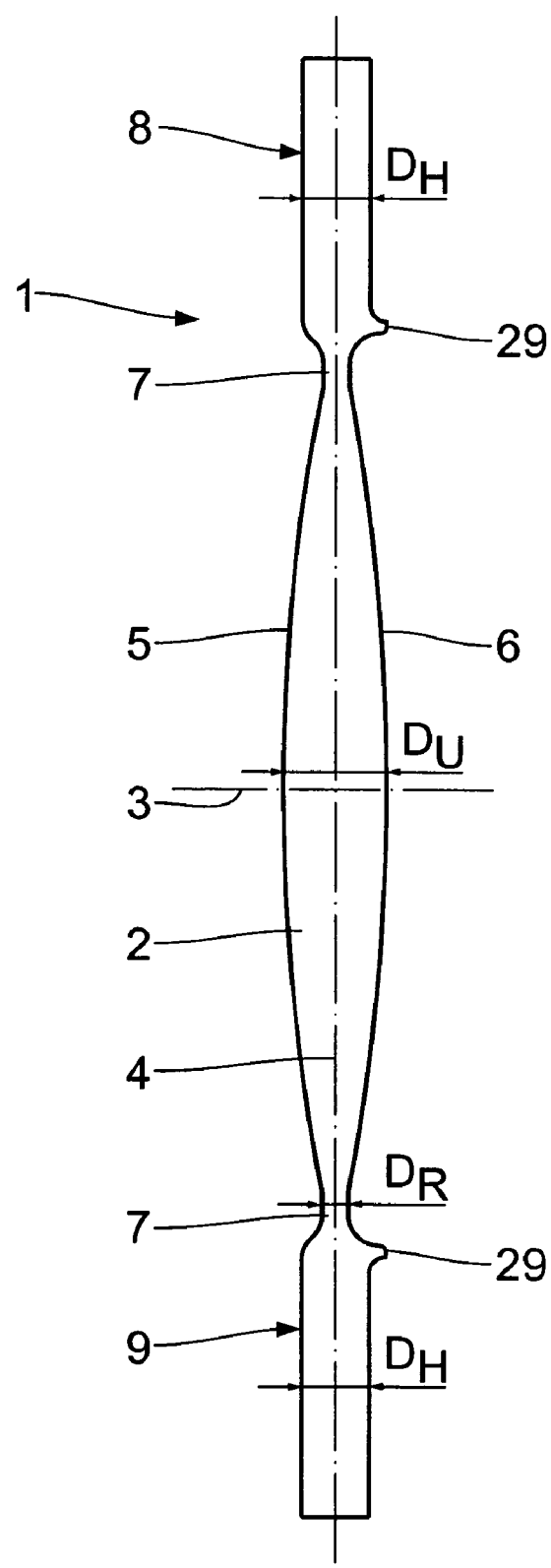
FIG. 3 is a cross-sectional view on the line III—III of FIG. 1.
Figure 3A:
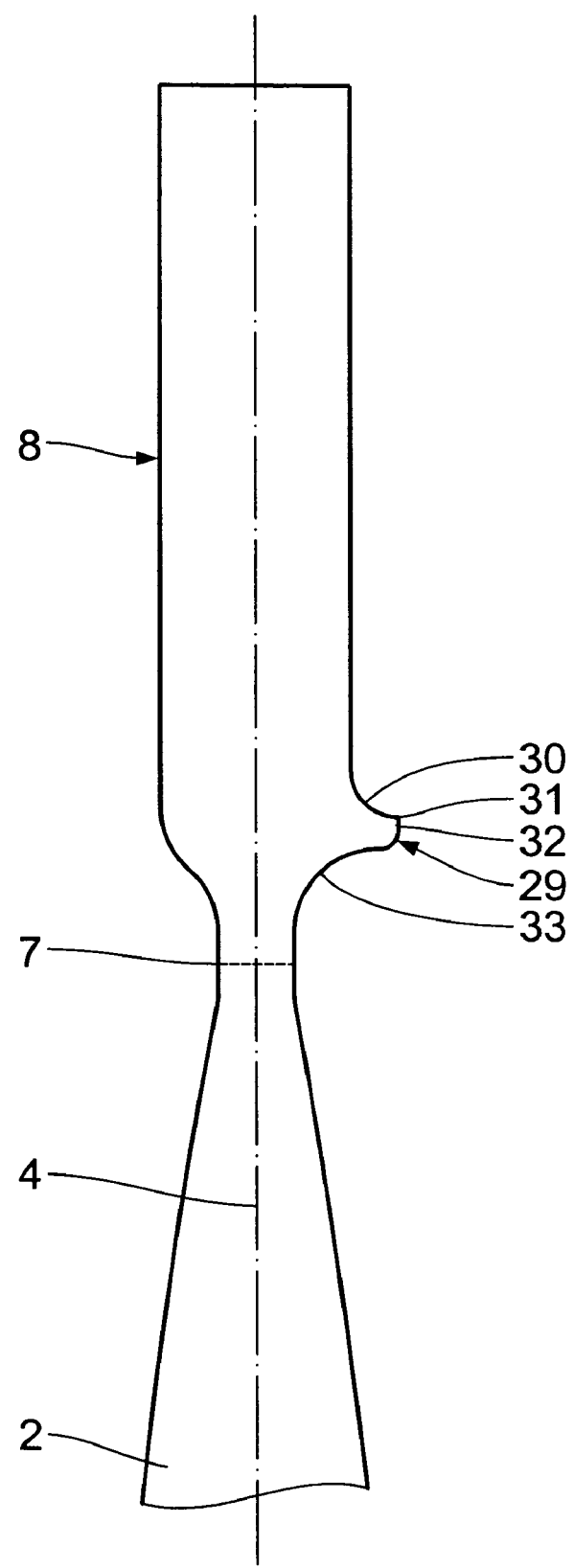
FIG. 3a is an enlarged view of details of an area of FIG. 3.

As seen in FIG. 3, the anterior surface 5 and the posterior surface 6 are convex in relation to the lens plane 4 i.e., they bulge outwards. The thickness $D_U$ of the optic 2 in the vicinity of the axis 3 depends on the required refractivity of the lens. The thickness decreases continuously from the middle to the rim 7. An area $D_R$ of minimal thickness results in the vicinity of the rim, with $D_R = 0.18$ mm applying. The haptics 8 and 9 that adjoin the rim 7 have a constant thickness $D_H$ in the axial direction, to which $D_H \cong 0.44$ mm applies. Consequently, $1.5 \leq D_H/D_R \leq 3.5$ applies, in particular $D_H/D_R \cong 2.5$. Noticeably, the thickness $D_H$ of the haptics 8, 9 in the vicinity of the pre-determined bending points 21, 22 exceeds the width $B_S$ of the haptic clamps 10, 11 in the vicinity of the pre-determined bending points 21, 22. $1.2 \cong D_H/B_S \leq 2.5$ applies, and in particular $D_H/B_S \cong 1.7$. The thickness $D_H$ of the connecting clamp 27 exceeds the width $B_V$ thereof, with $1.5 \leq D_H/B_V \leq 3$ applying, in particular $D_H/B_V \cong 2.2$. The fact that, in the vicinity of the flexible elements i.e., the pre-determined bending points 21 and 22 as well as the connecting clamp 27, the thickness of the material exceeds the width thereof ensures that, upon deformation in reaction to forces acting on the haptics 8 and 9 radially from outside, the haptics 8, 9 will deform in the lens plane 4 without the optic 2 escaping in the posterior or anterior direction.

On the posterior side of the lens 1 i.e., to the right in FIG. 3, a cell barrier 29 is located between the rim 7 and the haptics 8, 9, projecting axially. The cell barrier 29 has the shape of a segment of an arc of a circle and is disposed in the entire area of transition from the inner clamp 12 to the central clamp 13. As seen radially from the outside inwardly, the cell barrier 29 comprises a continuously ascending flank 30 of constant curvature. At the peak of the barrier 29, the flank 30 ends, forming a sharp edge 31. As seen from the plane 4, the barrier 29 has a convex section 32 of constant curvature that proceeds from the edge 31 and passes continuously into a concave section 33 of different, but substantially constant curvature. The cell barrier 29, after implantation of the lens 1, prevents cells of the epithelium of the lens, which are still in the capsule after removal of the natural lens, from spreading from the equatorial area of the capsule inwards in parallel to the surface of the haptics 8 and 9 and as far as to the optic 2, leading to decreasing transparency in the vicinity of the optic. They will be stopped at the barrier 29 at the latest. The sharp edge 31 is particularly important in this case. It is possible to make all the outer edges of the intraocular lens sharp so as to avoid any undesired growth of cells.

The following is a description of the implantation of the intraocular lens 1 with a view to the required properties of deformation of the lens. FIGS. 1 to 3a show the intraocular lens 1 in a condition without stress. The intraocular lens 1 is for example made by machining from transparent acrylate. The material is hard when worked.

Then the intermediate product is put into an aqueous sodium chloride solution where the acrylate absorbs water and becomes flexible. This material is called pHEMA, polyhydroxy ethyl methacrylate. It is reversibly deformable. Other materials may be used as well. This means that, after deformation for example by compression of the haptics, the material will regain its original state once the action from outside stops. FIGS. 1 to 3a illustrate the stressfree condition of a flexible intraocular lens 1. If the natural lens in the human eye becomes clouded as a result of disease, the lens will be removed with the surrounding capsule remaining. To this end, the capsule will be provided with a circular hole. For implantation, the lens 1 seen in FIGS. 1 to 3a is being compressed and inserted through the hole into the capsule where it expands until the outer contours 23 of the haptics 8 and 9 rest on the inward rim 34 of the capsule in the equatorial area thereof as seen in FIG. 4.

Figure 4:
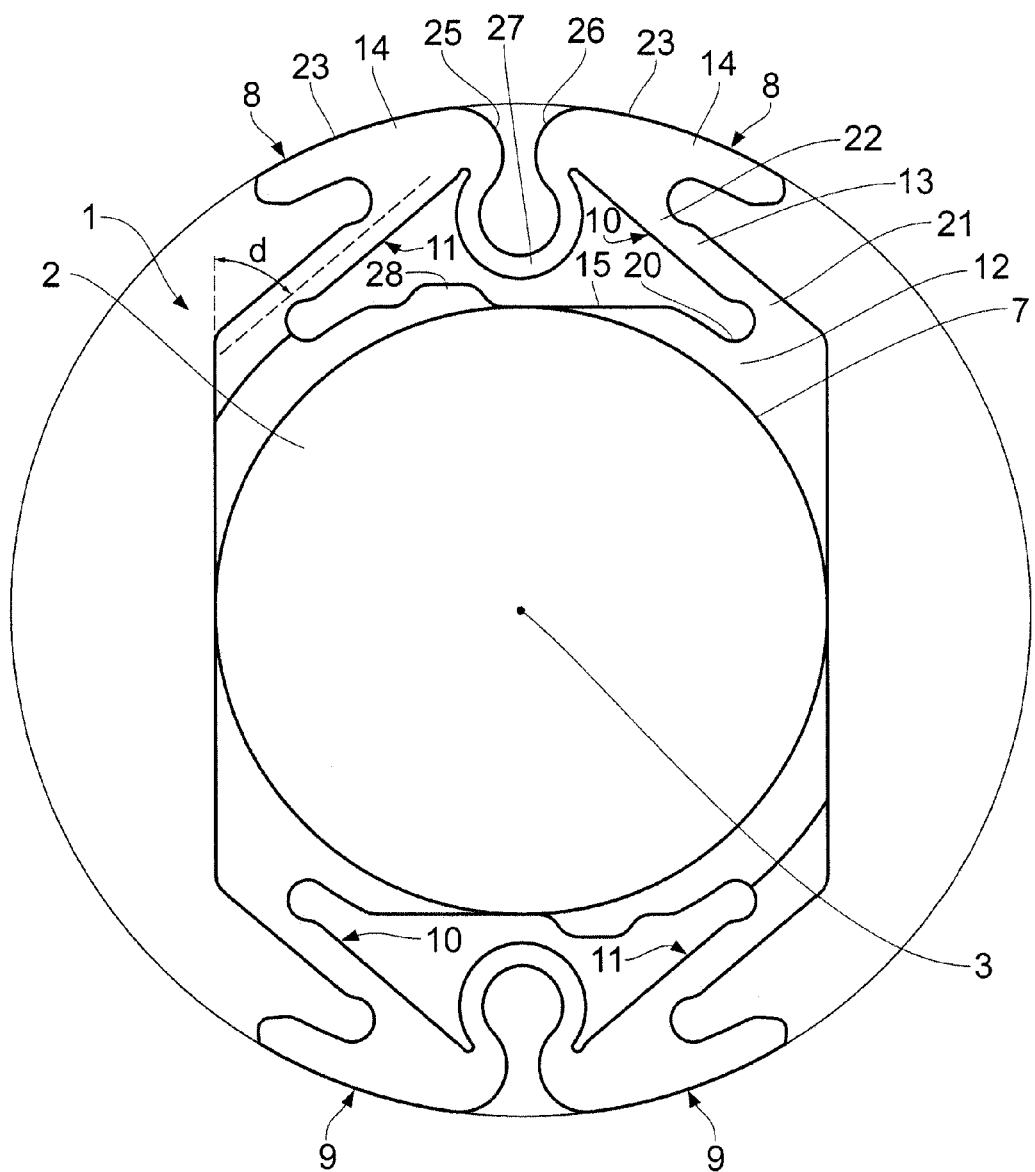
FIG. 4 is a view of the intraocular lens according to FIG. 1 with the haptics compressed.

A comparison of FIGS. 1 and 4 show the deformation behaviour of the haptics 8 and 9 with forces acting on them radially from outside. The predetermined bending point 21 provides for the central clamp 13 to be pivoted towards the plane 17 without losing its substantially straight shape. This increases the angle d. The pre-determined bending point 22 ensures that pivoting the central clamp 13 relative to the outer clamp 14 in the vicinity of the pre-determined bending point 22 is possible without the two clamps 13, 14 being deformed. The outer contour 23 of the outer clamps 14 rests full-face on the circular rim 34 of the capsule even in the deformed condition seen in FIG. 4. Compressing the haptics 8 and 9 results in the connecting clamp 27 being bent more strongly, more and more taking the shape of a near semi-circle. The comparatively small width $B_V$ of the connecting clamp 27 ensures that the clamp 27 itself is deformed and not any other surrounding parts. On the whole, the design of the haptics 8 and 9 has the advantage that the intraocular lens 1 can be used for capsules of various inside diameters without any risk of the optic tilting axially. The front and rear capsular leaf are able to glue together through the hole in each haptic, which ensures additional fixing of the intraocular lens 1.

What is claimed is:
1. An intraocular lens for implantation in a capsule of an eye, comprising:
   a. an optic which has
      i. a circular rim,
      ii. an optical axis, and
      iii. a lens plane which extends vertically of the optical axis;
   b. at least two haptics for support of the optic on the capsule, the haptics being fixed to the optic and forming one piece with the optic and consisting of reversibly deformable material, each haptic having
  i. a first Z-shaped haptic clamp connected to the rim,
  ii. a second Z-shaped haptic clamp connected to the rim, and
  iii. a concave connecting clamp which curves inwards in relation to the optical axis, connecting the first haptic clamp and the second haptic clamp,
c. wherein the first haptic clamp comprises a first inner joint and the second haptic clamp comprises a second inner joint, whereby in the vicinity of the inner joints the material of the haptic clamps has an inferior width $B_s$ as compared to the surrounding material,
d. wherein each haptic clamp comprises an inner clamp, which has substantially the shape of a partial ring that extends outward from the rim, angle at center b whereby $90° \geq b \geq 30°$,
e. wherein each inner clamp is integrally connected with the corresponding section of the rim along an angle b whereby $90° \geq b \geq 30°$,
f. wherein each inner clamp is defined by outer edges at both ends, the edges being substantially tangential to the rim,
g. wherein each haptic clamp comprises an outer clamp, which has a projecting free end,
h. wherein each haptic has a thickness $D_H$ whereby the thickness $D_H$ exceeds the width $B_s$ of each haptic claim in the vicinity of the inner joints.

2. An intraocular lens according to claim 1, wherein the intraocular lens is point-symmetric in relation to the optical axis.

3. An intraocular lens according to claim 1, wherein each haptic clamp further comprises a central clamp.

4. An intraocular lens according to claim 3, wherein said inner joints connect the central clamp to the inner clamps.

5. An intraocular lens according to claim 3, wherein the outer clamp is articulated to the central clamp by an outer joint.

6. An intraocular lens according to claim 5, wherein the outer clamp has a radially outward outer contour which is located substantially on an arc about the optical axis.

7. An intraocular lens according to claim 1, wherein the connecting clamp has an axial thickness $D_H$ and, in the lens plane, a width $B_v$, whereby $D_H$ is greater than $B_v$.

8. An intraocular lens according to claim 1, wherein the haptics comprise cell barriers that project outwards crosswise of the lens plane, serving to prevent cell migration.

9. An intraocular lens according to claim 1, wherein the haptics comprise cell barriers that project outwards perpendicularly of the lens plane, serving to prevent cell migration.

10. An intraocular lens according to claim 1, wherein an orienting means of asymmetrical arrangement is provided, for distinctly positioning the intraocular lens in the capsule.

11. An intraocular lens for implantation in a capsule of an eye, the intraocular lens comprising:
  an optic having a circular rim and a defined lens plane, said optic having an optical axis in an axial direction of said optic, said optical axis being perpendicular to said lens plane; and
  haptics fixed to said optic for supporting said optic on the capsule, said haptics being formed of reversibly deformable material, each haptic having a first Z-shaped haptic clamp, a second Z-shaped haptic clamp and a connecting clamp, said connecting clamp being concave and curving inward with respect to said optical axis, said concave connecting clamp connecting said first Z-shaped haptic clamp and said second Z-shaped haptic clamp, said first Z-shaped haptic clamp being connected to said circular rim and comprises a first inner joint, said second Z-shaped haptic clamp connected to said circular rim and comprises a second inner joint, material of said first and said second haptic clamp in the area of said first and said second inner joint having a width $B_s$ smaller than that of surrounding material, said first Z-shaped haptic clamp and said second Z-shaped haptic clamp comprising an inner clamp fixed to said circular rim, said inner clamp extending along a contour of said circular rim at an angle b with $90° \geq b \geq 30°$, said inner clamp having outer edges tangential to said circular rim, said first Z-shaped haptic clamp and said second Z-shaped haptic clamp further comprising an outer clamp having a projecting free end, each haptic having a thickness $D_H$ and a width $B_s$ in an area of said first inner joint and said second inner joint, whereby said thickness $D_H$ exceeds said width $B_S$.

12. An intraocular lens for implantation in a capsule of an eye, the intraocular lens comprising:
  an optic having a circular rim and a defined lens plane, said optic having a cutting plane defined in a longitudinal direction of said lens, said lens having an optical axis defined in an axial direction of said optic, said optical axis and cutting plane being perpendicular to said lens plane; and
  haptics fixed to said optic for supporting said optic on the capsule, said haptics being formed of reversibly deformable material, each haptic having a first Z-shaped haptic clamp, a second Z-shaped haptic clamp and a connecting clamp, said connecting clamp being concave and curving inward with respect to said optical axis, said concave connecting clamp connecting said first Z-shaped haptic clamp and said second Z-shaped haptic clamp, said first Z-shaped haptic clamp and said second Z-shaped haptic clamp comprising an inner clamp, said inner clamp being fixed to said circular rim, said inner clamp extending along a contour of said circular rim along an angle b with $30° \leq b \leq 90°$, said inner clamp having outer edges tangential to said circular rim, at least one outer edge being parallel to said cutting plane, said first Z-shaped haptic clamp and said second Z-shaped haptic clamp comprising an outer clamp having a projecting free end, said first Z-shaped haptic clamp and said second Z-shaped haptic clamp having a central clamp having a central axis, said central clamp being offset by an angle d defined by said outer edge and said central axis of said central clamp with $25° \leq d \leq 60°$, said central clamp being connected to said outer clamp such that said projecting free end is spaced apart from said central clamp portion, said first Z-shaped haptic clamp further comprising a first inner joint, said second Z-shaped haptic clamp further comprising a second inner joint.

* * * * *